(12) United States Patent
Grendze et al.

(10) Patent No.: US 6,420,439 B1
(45) Date of Patent: Jul. 16, 2002

(54) CROSSLINKED, NON-SWELLABLE AMPHOLYTIC BASE RESINS

(75) Inventors: Martin Grendze, Indianapolis; Donald W. McQuigg, Plainfield; John T. Wyeth, Indianapolis; Ernest Crowe, Beech Grove; Katherine M. Weisheit, Lafayette; Eric F. V. Scriven, Greenwood, all of IN (US)

(73) Assignee: Reilly Industries, Inc., Indianapolis, IN (US)

( * ) Notice: Subject to any disclaimer, the term of this patent is extended or adjusted under 35 U.S.C. 154(b) by 0 days.

(21) Appl. No.: 09/292,642

(22) Filed: Apr. 15, 1999

Related U.S. Application Data

(60) Provisional application No. 60/081,837, filed on Apr. 15, 1998, and provisional application No. 60/081,956, filed on Apr. 15, 1998.

(51) Int. Cl.[7] .............................. C08F 8/44; C08F 8/02; C08F 8/06; C08F 8/34
(52) U.S. Cl. .............................. 521/31; 521/33; 521/34; 521/38; 525/327.1; 525/344; 525/353; 525/359.2; 525/359.3; 525/359.4; 525/359.5; 525/387
(58) Field of Search .............................. 521/31, 38, 33, 521/34; 525/327.1, 359.4, 359.3, 359.5, 359.234, 353, 387

(56) References Cited

U.S. PATENT DOCUMENTS

| | | | |
|---|---|---|---|
| 4,323,702 A | 4/1982 | Kawabata et al. | 562/485 |
| 4,522,726 A | 6/1985 | Berry et al. | 210/660 |
| 4,552,905 A | 11/1985 | Keil et al. | 521/149 |
| 4,720,579 A | 1/1988 | Kulprathipanja | 562/580 |
| 4,764,276 A | 8/1988 | Berry et al. | 210/264 |
| 4,808,317 A | 2/1989 | Berry et al. | 210/660 |
| 4,851,573 A | 7/1989 | Kulprathipanja et al. | 562/580 |
| 4,851,574 A | 7/1989 | Kulprathipanja | 562/580 |
| 5,032,686 A | 7/1991 | Duflot et al. | 562/580 |
| 5,382,681 A | 1/1995 | Derez et al. | 562/580 |
| 5,412,126 A | 5/1995 | King et al. | 554/185 |
| 5,604,264 A | 2/1997 | McQuigg | 521/38 |
| 5,693,680 A | 12/1997 | McQuigg | 521/30 |

FOREIGN PATENT DOCUMENTS

| | | | |
|---|---|---|---|
| CS | 255497 | 12/1988 | B01J/43/00 |
| WO | Wo 92/16490 | 10/1992 | C07C/51/47 |
| WO | WO 92/16534 | 10/1992 | C07F/9/117 |
| WO | WO 93/06226 | 4/1993 | C12P/7/56 |
| WO | WO 97/13569 | 4/1997 | B01D/15/08 |
| ZA | 855155 | 7/1985 | |

OTHER PUBLICATIONS

Juracka, Chem Abstracts, 111:155, 489 (1988).*
Helfferich, "Ion Exchange", McGraw–Hill Cook Co., Inc. New York, pp. 76–77, 105 (1962).*
Whelan, "Polymer Technology Dictionary", 2$^{nd}$ ed., Chapman & Hall, New York, p. 100 (1994).*
Advanced Separation Technolgies Incorporated™, "ISEP® System L100 Laboratory Model: Continuous Sorption From Advanced Separation Technologies Inc.".
Advanced Separation Technolgies™, "The ISEP® Principle Of Continuous Adsorption".

* cited by examiner

*Primary Examiner*—D. R. Wilson
(74) *Attorney, Agent, or Firm*—Woodard, Emhardt, Naughton, Moriarty & McNett

(57) ABSTRACT

Described are non-swelling, crosslinked, bead forms of ampholytic base polymers that can be utilized in the chromatographic-type separation of acids from other compounds. Preferred polymers are prepared by modifying a poly-2 or poly-4-vinylpyridine resin crosslinked with divinylbenzene.

16 Claims, 10 Drawing Sheets

CROSSLINKED, NON-SWELLABLE AMPHOLYTIC BASE RESINS

REFERENCE TO RELATED APPLICATIONS

This application claims priority to U.S. Patent Application Serial Nos. 60/081,837 and 60/081,956 both filed Apr. 15, 1998, each of which is hereby incorporated by reference in its entirety.

BACKGROUND OF THE INVENTION

The present invention resides generally in the field of separations of acids from other compounds, and polymers useful for such separations. In particular, the invention relates to the separation of acids from other compounds using ampholytic base polymers.

It is often necessary to separate acidic compounds such as carboxylic acids from other compounds by treating mediums containing their admixture. As examples, citric and lactic acid are manufactured by fermentation in large scale worldwide. Such fermentations provide broths containing sugars and other compounds from which the desired acids must be separated for downstream use. Where such high volume manufacture is undertaken, it is extremely important to keep product recovery costs to a minimum.

Recent recovery work has focused on the use of solid polymeric materials to separate carboxylic acids from other components of fermentation broths. In this approach, the fermentation broth is treated with the solid polymer in a liquid-solid interaction which results in the separation of the acid from the other broth components. To date, a variety of solid polymers for such liquid-solid separation processes have been proposed.

For example, Kawabata et al., in U.S. Pat. No. 4,323,702, describe a process for recovering carboxylic acids with a material of which the main component is a polymeric adsorbent having a pyridine skeletal structure and a cross-linked structure. The carboxylic acid is adsorbed on the adsorbent, and then desorbed using a polar organic material such as an aliphatic alcohol, ketone or ester.

Kulprathipanja et al., in U.S. Pat. Nos. 4,720,579, 4,851,573, and 4,851,574, teach the use of solid adsorbents including a neutral, nonionegic, macroreticular, water-insoluble cross-linked styrene-poly(vinyl)benzene, a cross-linked acrylic or styrene resin matrix having attached tertiary amine functional groups or pyridine functional groups, or a cross-linked acrylic or styrene resin matrix having attached aliphatic quaternary amine functional groups.

South African Patent Application No. 855155, filed Jul. 9, 1985, describes other processes in which acids were recovered from their aqueous solutions. In an adsorption step, the acid-containing solution was passed through a column containing an adsorber resin consisting of a vinylimidazole/methylene-bis-acrylamide polymer, a vinylpyridine/trimethylolpropane tri-methacrylate/vinyltrimethylsilane polymer, a vinylimidazole/N-vinyl-N-methylacetamide/methylene-bis-acrylamide polymer, Amberlite IRA 35 (Rohm & Haas-acrylate/divinylbenzene based polymer containing dimethylamino groups), or Amberlite IRA 93 SP (Rohm & Haas) or Dowex MWA-1 or WGR-2 (Dow Chemical) (these latter three being styrene/divinylbenzene based polymers containing dimethylamino groups). To desorb the acid, water, usually at a temperature of 90° C., was allowed to pass through the column.

International Applications PCT/US92/02107 filed Mar. 12, 1992 (published Oct. 1, 1992, WO 92/16534) and PCT/US92/01986 filed Mar. 12, 1992 (published Oct. 1, 1992, WO 92/16490) both by Reilly Industries, Inc., disclose recovering lactic and citric acid, respectively, using a divinylbenzene crosslinked vinylpyridine or other similar resin.

U.S. Pat. No. 5,412,126 describes processes in which citric acid is adsorbed on a base resin and then stripped using an alkylamine. The free acid is recovered by dewatering the material and driving the amine off with heat. U.S. Pat. No. 5,032,686 describes a process in which citric acid is separated from sugars using an acid resin, whereas U.S. Pat. No. 5,382,681 describes a process in which a citric acid solution containing another compound is first treated with base to convert the citric acid to trisodium citrate, whereafter the basic medium is passed over a base resin to separate other compounds.

Czechoslovakian Inventor's Certificate No. 255497 B1, published on Jul. 16, 1997 and granted on Dec. 15, 1988, describes the use of a swellable resin containing carboxymethylpyridine functional groups to sorb anions and cations.

Despite the above-described work, there remain needs for improved, effective processes for treating mediums to separating acids from other compounds. The present invention addresses these needs.

SUMMARY OF THE INVENTION

A feature of the invention is the discovery that ampholytic base polymers can be used with advantage to treat mediums to chromatographically separate acids from other compounds. Accordingly, a preferred embodiment of the invention provides a process for treating a medium to separate at least one acid from at least one other compound, which includes contacting the medium with an ampholytic base polymer under conditions effective to separate the acid(s) from the other compounds. Preferred processes of the invention are chromatographic in nature, and involve separations achieved using a solid stationary phase containing an ampholytic base polymer. The ampholytic base polymer used in the present invention can include individual repeating units carrying both a positive and negative charge (so-called ampholytic inner salts), or alternatively or in addition can include some repeating units carrying only a negative charge and some repeating units carrying only a positive charge (so-called ampholytic ion pairs). Desirable ampholytic base polymers for purposes of the present invention include, for example, those encompassed by the formula

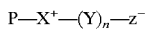

wherein P represents a polymer backbone, $X^+$ is a positively-charged group, Y is a linking group covalently linking $X^+$ and $Z^-$, n=0 or 1, and $Z^-$ is a negatively-charged group. The ampholytic functions $—X^+—(Y)_n—Z^-$ are preferably provided by pendant functions containing positively-charged tetravalent nitrogens (i.e. $N^+$) wherein the nitrogens are covalently bonded to negatively-charged groups $—(Y)_n—Z^-$. Thus, preferred stationary phases for use in the invention have pendant functions containing the group

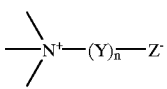

The tetravalent nitrogen, $N^+$, can occur in a cyclic amino group or an acyclic amino group. In certain preferred polymers for use in the invention, this nitrogen occurs in a heterocyclic ring, such as that provided by modified pyridyl groups of polyvinylpyridines, especially 2- or 4-vinylpyridines.

Particularly preferred inventive processes employ a continuous contacting apparatus including a plurality of contacting zones (e.g. columns) filled with the ampholytic base polymer. A separation zone is established including a plurality of the contacting zones together containing a sufficient amount of the polymer to achieve substantial separation of the acid(s) from the other compound(s) in the medium. An elution zone is also established after achieving such separation, from which a product eluent is obtained containing either the acid(s) or the other compound(s).

For example, in a process for recovering an acid from a fermentation broth, the product eluent will contain the fermentively-produced acid separated from other undesirable components of the fermentation broth, for example sugars. On the other hand, in a process for removing an acid impurity from a sugar product, the product eluent will contain the sugar separated from the acid impurity.

A still more preferred manner of carrying out processes of the invention includes the steps of:

(a) providing a plurality of contacting zones containing an ampholytic base polymer;

(b) sequentially processing the contacting zones through a chromatographic separation zone wherein an eluent solution and an aqueous solution containing the acid and the other compound(s) are together passed through the contacting zones to chromatographically separate the acid from the other compound(s); and (c) after step (b), sequentially processing the contacting zones through an elution zone so as to elute the desired product (the acid(s) or the other compound(s)) from the one or more contacting zones in a solution of the eluent. In advantageous processes, the eluent is water.

Another embodiment of the invention provides a polymer useful for the separation of an acid, comprising a bead-form, crosslinked polymer having repeating units selected from the group consisting of Formula I, Formula II and Formula III below:

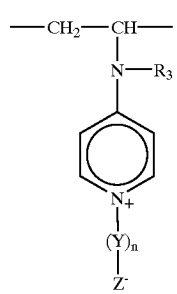

Formula I

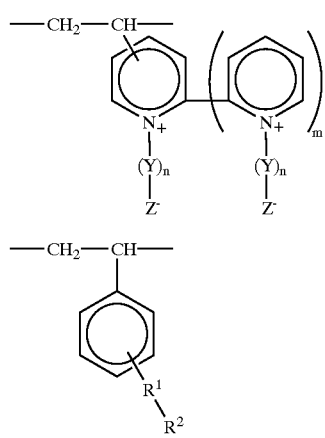

Formula II

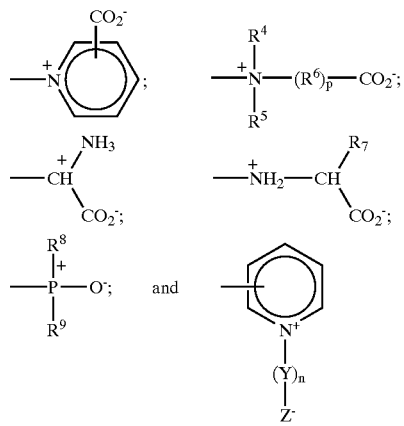

Formula III wherein:
  m and n are each 0 or 1;
  Y and $Z^-$ are as defined above, with the proviso that when n is 0 in Formula I, $Z^-$ is not $O^-$ (i.e. excluding N-oxide derivatives from Formula I);
  $R^1$ is an organic group having from 1 to about 6 carbon atoms, optionally containing one or more nitrogen or oxygen atoms; especially an alkylene group having from 1 to about 6 carbon atoms;
  $R^2$ is an organic group having 1 to about 12 carbon atoms and containing a negatively-charged oxygen, boron or sulfur atom, and a positively-charged nitrogen or phosphorous atom; especially a group selected from wherein p is 0 or 1, $R^4$, $R^5$, $R^8$ and $R^9$ are alkyl groups, preferably having from 1 to about 6 carbon atoms, especially methyl, $R^6$ is an alkylene group, preferably having from 1 to about 6 carbon atoms, $R^7$ is an organic group such that the group —$NH_2$—$CH(R^7)$ ($CO_2^-$) represents an amino acid, and n, Y and $Z^-$ are as defined above; and
  $R^3$ is an alkyl group having 1 to about 6 carbon atoms, especially methyl.

The invention provides improved methods for separating acids from other compound(s), utilizing ampholytic base polymers, and also novel ampholytic base polymers useful for such separations. The preferred methods and polymers of the invention enable the conduct of improved procedures facilitating high levels of product recovery, and also not requiring the use of thermal swing conditions to achieve advantageous eluents having high product purity and concentration. Additional objects, as well as features and advantages of the invention, will be apparent from the following description.

DESCRIPTION OF THE PREFERRED EMBODIMENTS

Figure 1:
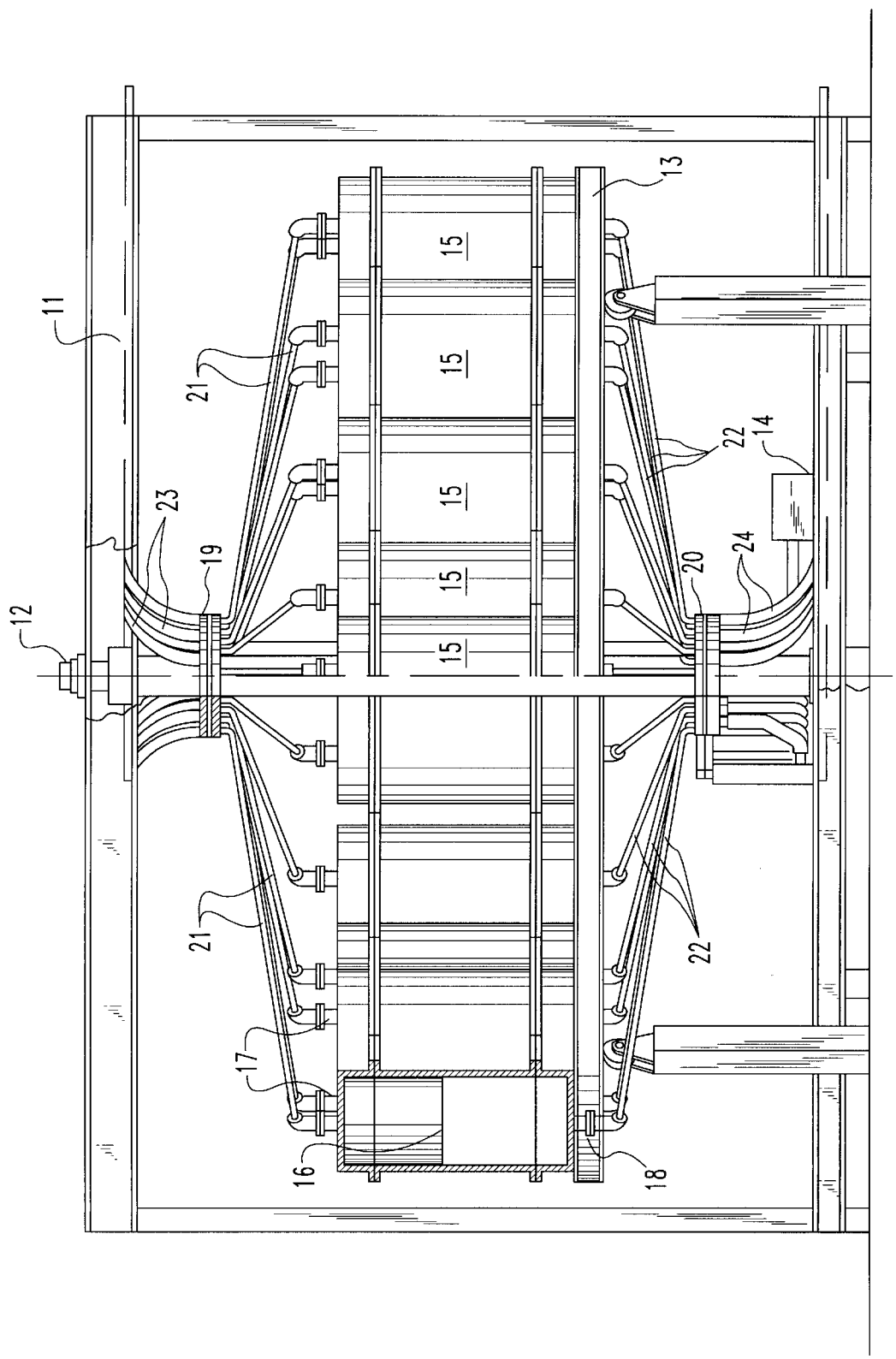
FIG. 1 is a side elevational view partially in cross-section of an illustrative continuous contacting apparatus which can be used in the present invention.
Figure 2:
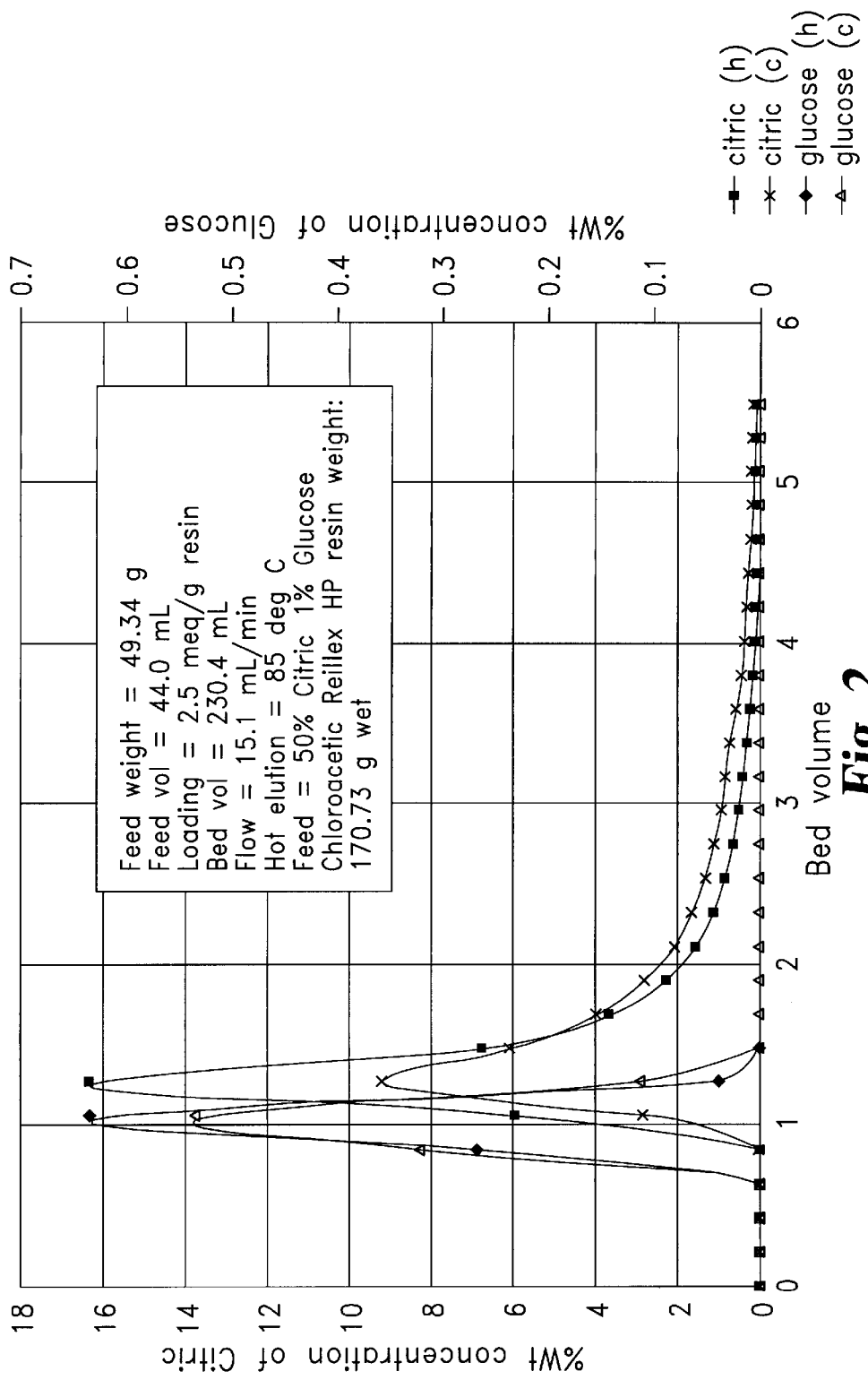
FIGS. 2–7 are chromatograms obtained in citric acid/glucose pulse testing over ampholytic base polymers in accordance with the invention, as described in Examples 2–7 below.
Figure 3:
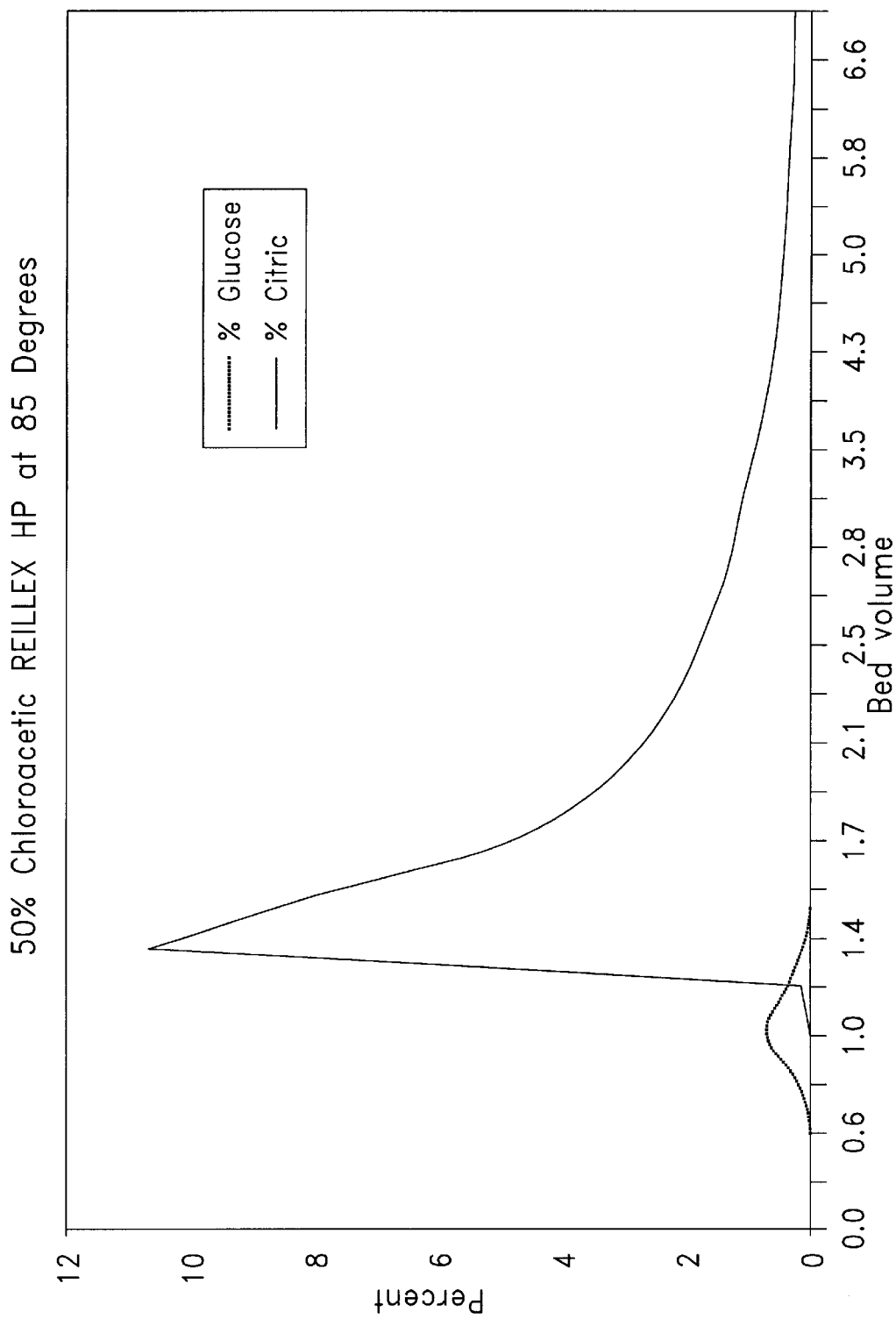
Figure 4:
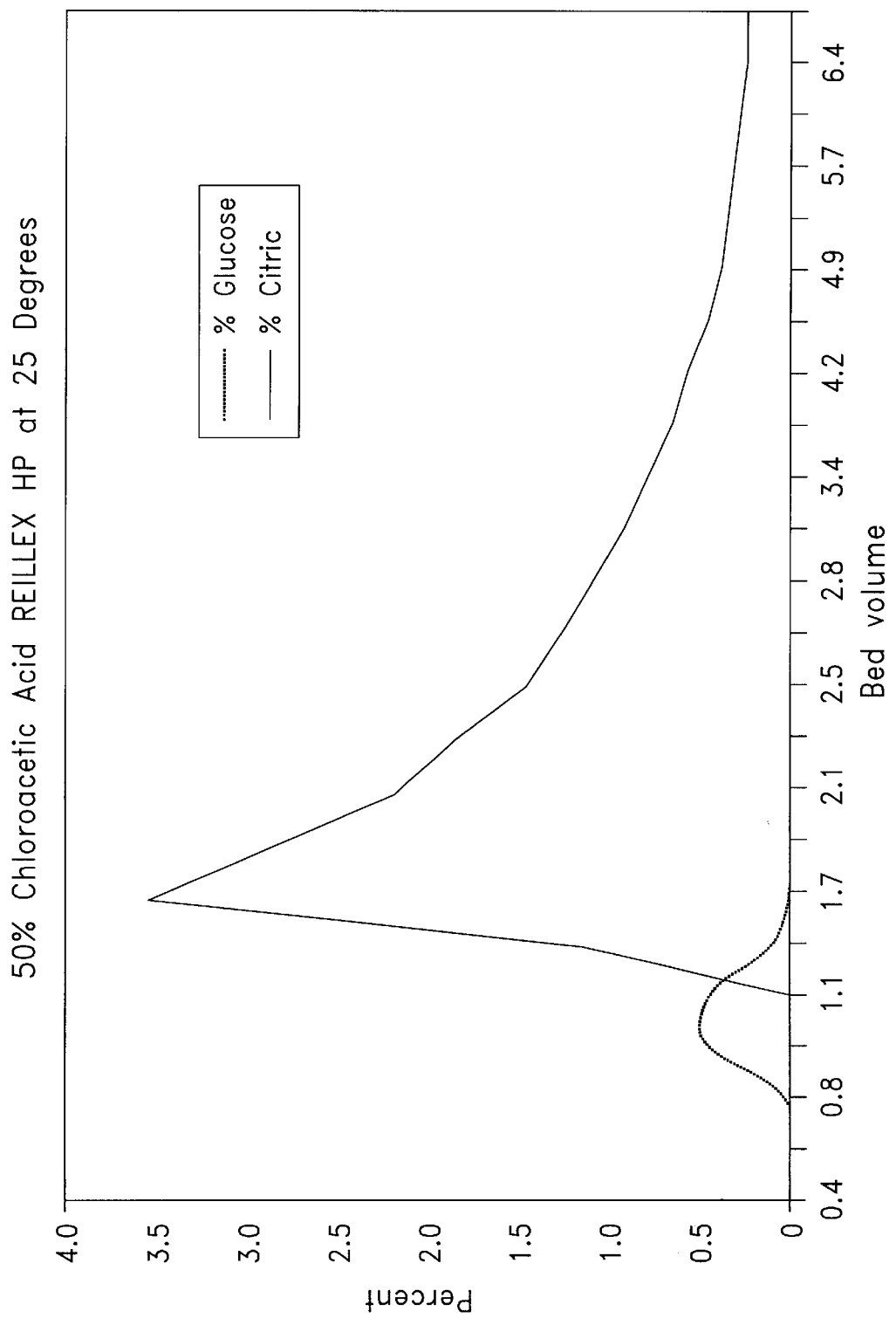
Figure 5:
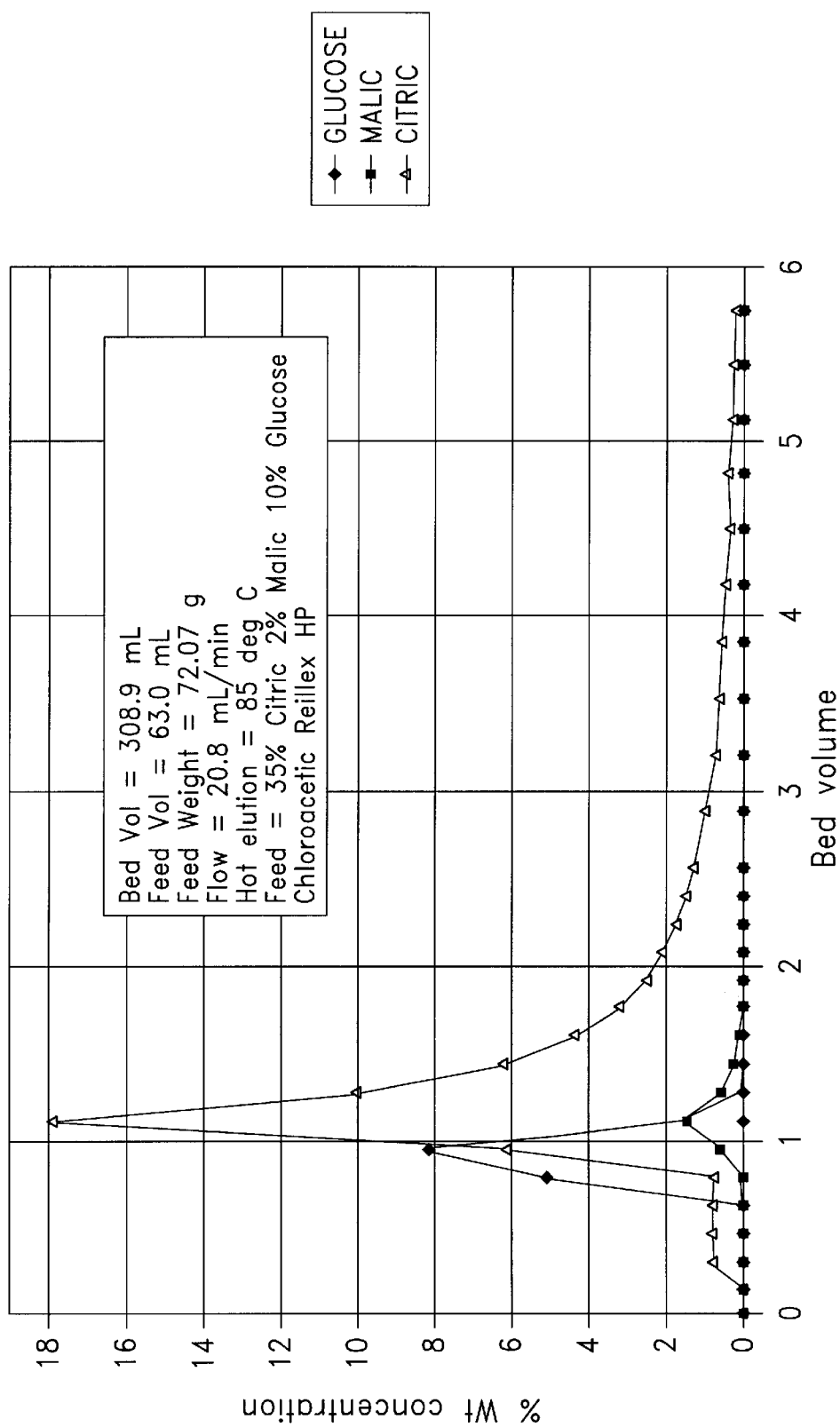
Figure 6:
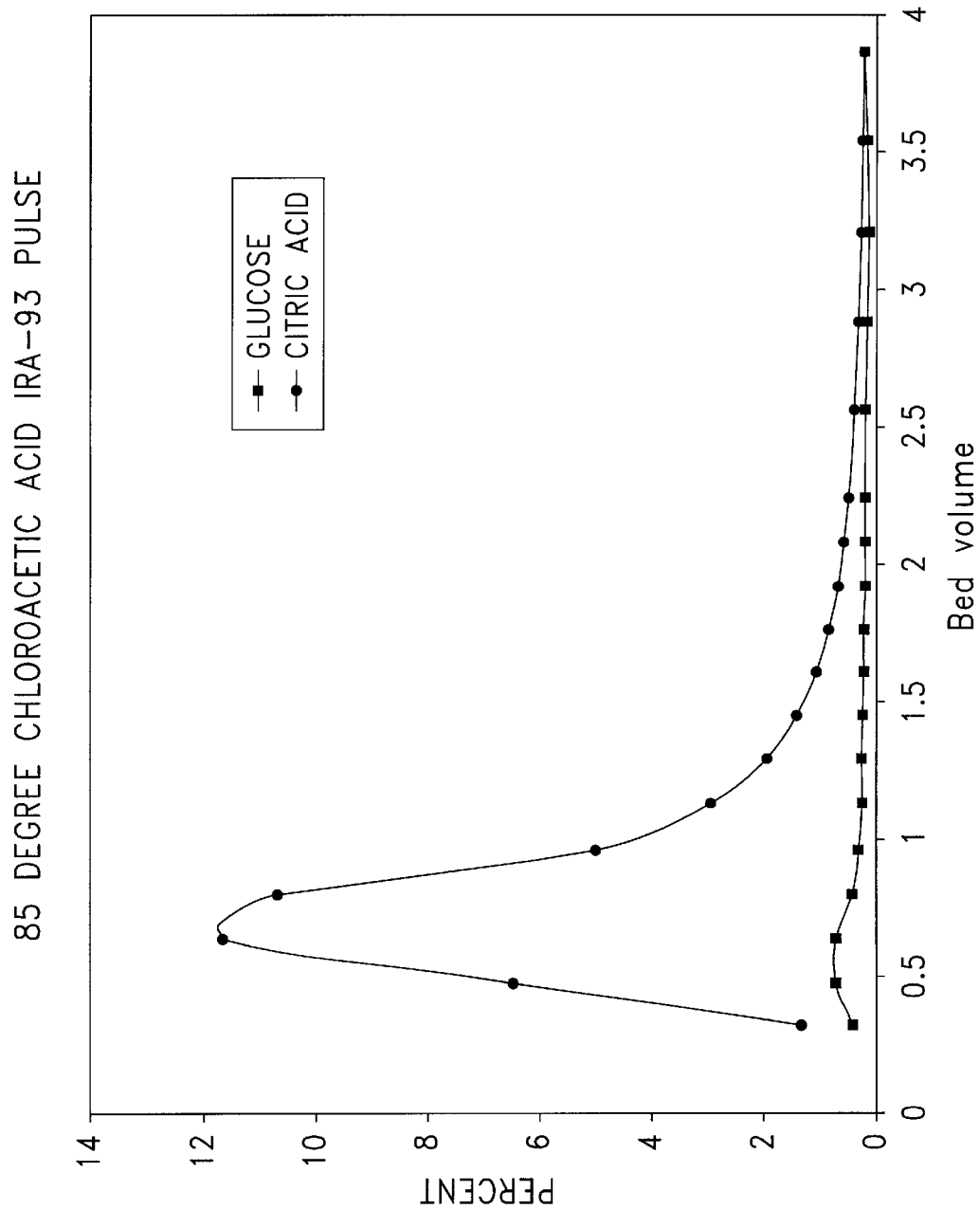
Figure 7:
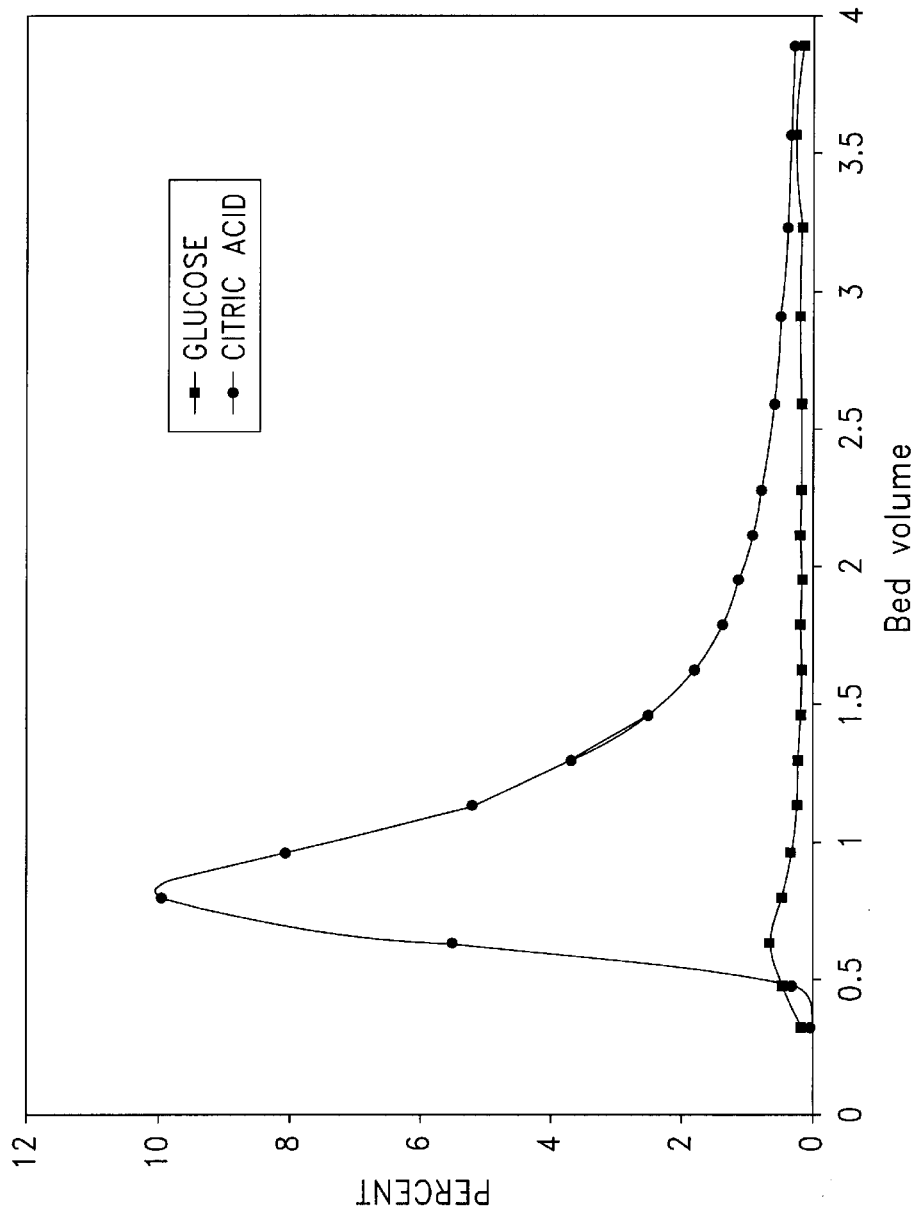

For the purposes of promoting an understanding of the principles of the invention, reference will now be made to certain of its embodiments and specific language will be used to describe the same. It will nevertheless be understood that no limitation of the scope of the invention is thereby intended, such alterations and modifications and applications of the principles of the invention as described herein being contemplated as would normally occur to one skilled in the art to which the invention pertains.

As indicated above, one preferred embodiment of the present invention provides processes for the separation of at least one acid from at least one other compound using an ampholytic base polymer. As is known, an ampholytic polymer is one which possesses both positively and negatively charged moieties. These positively and negatively charged groups can occur on the same pendant group, or on different (e.g. alternating) pendant groups. A feature of the present invention is the discovery that polymers which are generally basic in character (i.e. base polymers), and also ampholytic in character, have modified properties which provide for improved processes for separating acids from their admixture with other compounds.

For example, it has been found that ampholytic base polymers have moderated basic properties which improve chromatographic separations of acids and other compounds, providing increased product recovery, highly concentrated product eluents, and obviating or reducing the need to apply a thermal swing during separation and elution phases to achieve effective preparative-scale processes.

Generally speaking, the ampholytic base polymer employed in the invention will have an affinity for the acid(s) which is greater than that for the other compound(s), and will be stable (i.e. will not undergo substantial degradation) under the processing conditions utilized in the separation. Desirable ampholytic base polymers for use in the invention will be crosslinked to provide thermal and mechanical stability and an advantageous solid physical form which does not swell to any significant extent during the separation of the acid(s) from the other compound(s). Bead-form adsorbent resins are preferred, especially those having a particle size of about 20 to about 200 mesh, more especially about 40 to about 120 mesh.

A wide variety of base polymers have been reported for the separation of acids such as carboxylic or other acids, and with modification to provide polyampholytic character these base polymers can be used in processes of the present invention. These polymers are generally formed through the polymerization of one or more monomers and including a crosslinking monomer. The polymerization is carried out to provide resin beads in either gel or macroreticular form.

One set of preferred ampholytic base polymers for se in the present invention includes those encompassed y the general formula:

P—X⁺—(Y)ₙ—Z⁻ wherein P represents a polymer backbone; X⁺ is a positively-charged group; Y is a linking group covalently linking X⁺ and Z⁻, preferably an alkyl group having 1 to about 6 carbon atoms, optionally substituted one or more groups of the formula —NH₂ or —COOH; n=0 or 1; and Z⁻ is a negatively-charged group, preferably an organic group having from 1 to about 12 carbon atoms having a negatively-charged oxygen or boron atom. The ampholytic functions —X⁺—(Y)ₙ—Z⁻ are desirably provided by groups having a positively-charged tetravalent nitrogen (i.e. N⁺) covalently bonded to a negatively-charged group —(Y)ₙ—Z⁻. Thus, preferred stationary phases for use in the invention have pendant functions containing the group

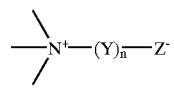

The tetravalent nitrogen, N⁺, can occur in a cyclic or acyclic amino group. In certain preferred polymers for use in the invention, this nitrogen occurs in an aromatic heterocyclic ring, such as that provided by modified pyridyl groups of polyvinylpyridines, especially modified poly-2- or poly-4-vinylpyridines. Alternatively, or in addition, the tetravalent nitrogen may be provided in a modified aliphatic amino group, such as a modified pendant dialkylamino group.

Given the teachings herein, it will be understood that a wide variety of ampholytic base polymers are available for use in the invention. Illustrative polymers include those having repeating units encompassed by Formulas I, II, III or IV below:

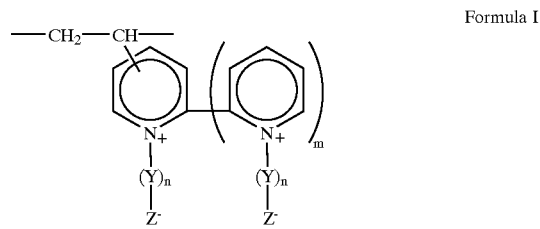

Formula I

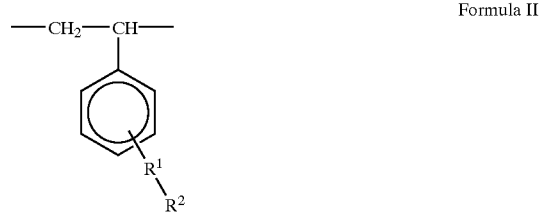

Formula II

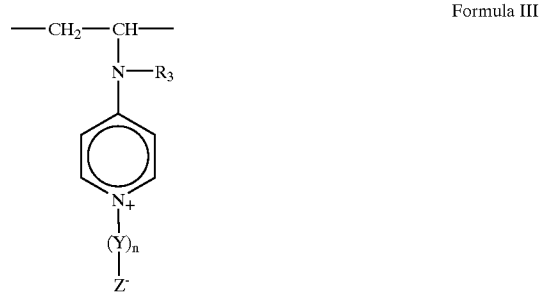

Formula III

Formula IV

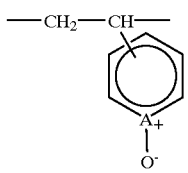

wherein:
n, Y and Z⁻ are as defined above, with the proviso that in Formula I when —Z⁻ is —O⁻, n is 1 (i.e. excluding the pyridine N-oxide derivatives from Formula I);
m=0 or 1;
$R^1$ is an organic group having from 1 to about 6 carbon atoms, optionally containing one or more nitrogen or oxygen atoms;
$R^2$ is an organic group having from 1 to about 12 carbon atoms and containing a negatively-charged oxygen, boron or sulfur atom, and a positively-charged nitrogen or phosphorous atom;
$R^3$ is an alkyl group having from 1 to about 6 carbon atoms; and
A is a heteroatom selected from N and P.

More preferred polymers are provided where m is 0 and n is 1. Also, Y and $R^1$ are preferably an alkylene group having 1 to 6 carbon atoms, optionally substituted with one or more amino (—NH$_2$) or carboxyl (—COOH) groups, especially —CH$_2$—; —CH$_2$CH$_2$; —CH(NH$_2$)—; or —CH(COOH)—. $R^2$ is desirably a group selected from:

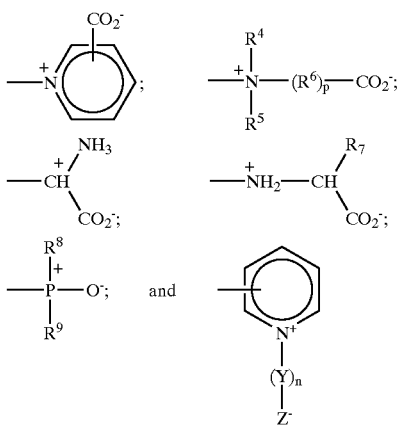

wherein p is 0 or 1, $R^4$, $R^5$, $R^8$ and $R^9$ are alkyl groups, preferably having from 1 to about 6 carbon atoms, especially methyl, $R^6$ is an alkylene group, preferably having from 1 to about 6 carbon atoms, $R^7$ is an organic group such that the group —NH$_2$—CH($R^7$) (CO$_2^-$) represents an amino acid, and n, Y and Z⁻ are as defined above.

In general, the ampholytic base polymer will contain substantial repeating units as identified herein so as to participate in providing the capacity to effectively separate the one or more acids from the one or more other compounds. For example, ampholytic base polymers that are at least about 10% by weight constituted by such identified repeating units are preferably employed, more preferably at least about 30% by weight, and most preferably at least about 50% by weight. Other monomeric units in the polymer may be derived, for example, from crosslinking monomers and/or other monomers which provide characteristics to the overall polymer consistent with its use in the separations described herein.

In one aspect of the invention, a base polymer in bead form can be chemically modified to provide ampholytic character to the polymer, e.g. by adding positive and negative ionic groups to repeating units of the resin. For example, a nitrogenous base polymer (e.g. carrying pendant pyridyl or aliphatic tertiary amino groups) can be quaternized to provide a polymer with repeating units generally as described above, wherein the N-bonded "quaternizing" group carries a negative charge, particularly on an atom such as an oxygen atom (e.g. as provided by a group —CO$_2^-$, SO$_3^-$ and the like) or a boron atom (e.g. as provided by a group —B(OH)$_3^-$). Nitrogenous polymers may also be N-oxidized so as to carry pendant functions containing the characteristic N-oxide function, N⁺—O⁻.

More preferred ampholytic base polymers for use in the invention are chemically modified, crosslinked pyridine-containing polymers, e.g. crosslinked vinylpyridine polymers. Particularly preferred pyridine-containing polymers are polyvinylpyridine polymers such as poly 2- and poly 4-vinylpyridine gel or macroreticular resins exhibiting a bead form, and which do not swell in the liquid (e.g. aqueous) medium involved in the separation. These resins are preferably at least about 15% cross-linked with a suitable cross-linking agent, such as divinylbenzene. Most preferred resins are chemically-modified, 15 to 50% crosslinked bead-form vinylpyridine polymers, e.g. poly 2- and poly 4-vinylpyridine polymers.

For example, these preferred resins include poly 2- and poly 4-vinylpyridine resins available from Reilly Industries, Inc., Indianapolis, Ind., in the REILLEX™ polymer series. These REILLEX™ polymers are generally crosslinked with divinylbenzene, and exhibit good thermal stability. Additional preferred resins are available from this same source under the REILLEX™ HP polymer series. For more information about these REILLEX™ polymers, reference can be made to the literature, including that available from Reilly Industries, Inc. in the form of REILLEX™ reports 1, 2 and 3.

Other resins, for example AMBERLYST A-21, AMBERLITE IRA 68, or AMBERLITE IRA 93 resins from Rohm and Haas, Philadelphia, Pa., or DOWEX MWA-1 resin from Dow Chemical, can also be chemically modified for use in the invention. Among these resins, the A-21 resin is crosslinked by divinylbenzene and contains aliphatic tertiary amine functions (particularly, attached dialkylamino (dimethylamino) groups); the IRA 68 resin contains aliphatic tertiary amine groups, a divinylbenzene-crosslinked acrylic matrix, and exhibits a gel form; and the IRA 93 and MWA-1 resins contain aliphatic tertiary amine groups, and are based on a divinylbenzene-crosslinked styrene matrix, exhibiting a macroreticular form. For additional information about these and other similar resins which can be used in the invention, reference can be made to the literature including that available from the manufacturers.

In other aspects of the invention, a starting polymer such as a crosslinked, haloalkylated (e.g. halomethylated) polystyrene resin, such as a crosslinked, chloromethylated polystyrene resin, can be reacted with an appropriate ligand to provide ampholytic base polymers of and for use in the invention. This synthetic approach can be used, for example, to prepare ampholytic base polymers having repeating units of the formula

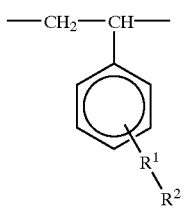

as described above, particularly where the group —R$^1$—R$^2$ occurs at the 3-position of the phenyl ring.

In featured processes of the invention, to separate at least one acid from at least one other compound in solution, a contacting zone is employed which contains an ampholytic base polymer which exhibits higher affinity for the acid(s) than the other compound(s). A first solution containing the acid(s) and the other compound(s) is introduced into the contacting zone. A second solution is introduced to the contacting zone along with the admixed acid(s) or other compound(s) solution to initiate a separation phase. For example, the second solution (eluent) can be water, an aqueous solution containing one of the acid(s) or other compound(s) but which is essentially free from the other, an organic solvent, or water and a water-miscible organic solvent such as an alcohol. The first and second solutions are processed in the contacting zone under conditions which are effective to establish a front of the acid(s) separated in the contacting zone from a front of the other compound(s). The front of acid(s) and/or of the other compound(s) is then eluted from the contacting zone in an elution phase. In this manner, a preferred chromatographic process is established which provides a recovered eluent purified in the acid(s) and/or in the other compound(s).

Processes of the invention can be carried out under non-isothermal conditions, in which the separation and elution phases are conducted at differing temperatures (e.g. with the elution zone temperature being elevated, for instance by at least about 10° C., relative to the separation zone temperature, as generally taught in WO97/13569, Apr. 17, 1997 (Reilly Industries, Inc.)). Preferably, however, processes of the invention are carried out under substantially isothermal conditions. In this regard, it has surprisingly been found that in preferred acid-recovery processes, a thermal swing is generally not necessary to establish high (e.g. 95%+) recovery of the acid in concentrated mediums when using an ampholytic base polymer. This enables the conduct of simplified processes in which equipment modifications to establish a thermal swing are not required.

As to the acids, preferred acids to which the present invention is applicable have pKa's in the range of about 2 to about 6, with one preferred group having pKa's of about 3 to about 5. Illustrative acids for use in the invention include, for example, aromatic acids such as phenol, salicylic acid, ortho-phthalic acid, meta-phthalic acid, benzoic acid, 3-chlorobenzoic acid; alpha-hydroxy acids such as citric acid, lactic acid, dilactic acid, malic acid, mandelic acid, benzilic acid, glyoxylic acid, glycolic acid, tartaric acid, formic acid, glutaric acid, fumaric acid, acetylacetic acid, acetic acid, succinic acid, itaconic acid; pyridinecarboxylic acids such as nicotinic acid or isonicotinic acid; piperidinecarboxylic acids such as isonipecotic acid; inorganic acids such as phosphoric acid, sulfonic acid, tungstic acid, molybdic acid, and the like. For additional background and identification of acids suitable for use in the present invention, reference can be made to the acids identified in U.S. Pat. Nos. 4,552,905, 4,323,702 and 5,412,126.

In accordance with the invention, acids can be separated from other, less-acidic compounds, including for example sugars, amino acids, amides (e.g. in the separation of carboxylic acids from corresponding amides), or other similar compounds with which the acids occur in nature or in industrial processing.

One particular aspect the invention is the recovery of organic acids, especially carboxylic acids such as aliphatic carboxylic acids, from mediums in which they have been produced by fermentation, i.e. by the fermentation of suitable carbon sources by microorganisms. For example, substantial worldwide production of organic carboxylic acids such as citric and lactic acids is performed by fermentation. In the case of citric acid, the broth may be from a fermentation of a carbon source such as corn sugar or molasses with suitable citric-acid-producing bacteria such as *Aspergillus Niger* or another microorganism. Lactic acid is produced using bacteria or other microorganisms capable of forming lactic acid upon metabolizing a carbon source. Typically, bacteria of the Family Lactobacillaceae are employed, although other microorganisms such as fungi may be used. For example, fungi of the family Rhizopus, such as *Rhizopus oryzae* NRRL 395 (United States Department of Agriculture, Peoria, Ill.), can be employed to produce substantially pure L+ lactic acid as generally taught in WO 93/06226, Apr. 1, 1993 (Reilly Industries, Inc.) It is well within the purview of the skilled artisan to select and use suitable fermentation organisms to produce fermentation broths containing organic acids such as carboxylic acids, which broths can be treated in accordance with the invention to recover the acids.

When a carboxylic acid-containing fermentation medium is involved, it will usually contain water, the product acid, salts, amino acids, sugars, and other various components in minor amounts. Such fermentation mediums can be filtered to remove suspended solids prior to processing over the ampholytic base polymer. In addition, in accordance with the present invention, the carboxylic acid-containing fermentation medium can be taken from an ongoing fermentation producing the carboxylic acid, and the removal of the acid can thereby be coupled to its fermentive production, for example as described for lactic acid in WO93/06226, Apr. 1, 1993 (Reilly Industries, Inc.). In such coupled processes, the feed into the separation process can be a portion of the fermentation medium, desirably after filtration or other treatments suitable for preparing the feed for passage into separation processes of the invention. The carboxylic acid is recovered by a separation process as described herein, and a carboxylic acid-depleted "waste" effluent stream from the separation process can be returned to the fermenter, thus returning nutrients for the fermentation. Such processes can effectively reduce feedback inhibition of the acid-producing cells by the acid product, for example as is known to occur in lactic acid fermentations.

A variety of liquid eluents can be employed in the present invention. These eluents include, for example, organic solvents, e.g. aromatic solvents or polar organic solvents such as alcohols (e.g. $C_1$–$C_5$ alcohols such as methanol, ethanol, propanol, isopropanol, butanol and methylisobutyl carbinol), ketones and esters, as well as aqueous mediums such as water (i.e. substantially pure water without added solutes), aqueous solutions of acids or bases, e.g. hydrochloric acid, sulfuric acid or sodium hydroxide solutions, or water/organic co-solvent mediums such as water/alcohol mixtures. Some preferred inventive processes employ water so as to provide acid-containing product eluents free from unnecessary solutes or co-solvents which may complicate recovery of the desired product. Other preferred inventive processes employ organic solvents such as alcohols in a fashion so as to dewater the acid product and recover the acid product in an organic solvent. When alcohols are used in such processes, the product can be recovered in alcohol with a minimal amount (e.g. less than 20% by weight, preferably less than 10% by weight) of water, and for example in the case of carboxylic acids (e.g. citric acid), the recovered product medium can be reacted in an esterification process to provide a corresponding carboxylic acid ester or partial ester.

In preferred chromatographic processes for purifying acids, concentrated feeds containing the acid at high levels are used. In some processes, acid levels which substantially exceed the capacity of the ampholytic base polymer may be used, e.g. exceeding such capacity by 20% or more, or even 100% or more. In this manner, when the feed is passed into the columns, a separation zone is established wherein there is more acid in the separation zone than the polymer in the separation zone has to capacity to capture. In this regard, the capacity of a material for a product of interest such as an acid is a well known expression, and can be determined, for example, by computing the difference in product captured by the material in contact with product in solution at constant concentration as shown in equilibrium isotherm diagrams. It will be understood that the particular acid feed concentration employed will be selected based upon various factors at hand, including for example the desire to maximize the use of the resin while at the same time achieving acid product streams of the requisite purity.

Thus, in more preferred processes for separating citric acid from impurities such as sugars, a concentrated solution of citric acid, for example having a concentration exceeding about 20%, more preferably exceeding 30%, is used as the product feed. The concentrated feed of citric acid can be obtained, for example, by concentrating a citric acid-containing aqueous medium from a fermentation initially having a citric acid level of less than 20%. This concentrating step can be accomplished in any acceptable fashion, for instance including evaporation of water from the medium. The thus concentrated medium, having an increased citric acid concentration, is then used as feed into the inventive processes.

In other processes of the invention, a medium containing the acid(s) and the other compound(s) will be treated with the primary interest of obtaining the other compound(s) in purified form, separated from the acid(s). For instance, many industrial processes are dedicated to removing acid(s) from sugar-containing mediums, such as sugar juices or syrups, including for example sugarcane juices and corn syrups. In accordance with the present invention, such sugar-containing solutions or mediums can be treated over an ampholytic base polymer, as described above, to separate acid(s) such as organic acids (e.g. amino acids) from the sugar(s), and recover a product stream containing the purified sugar(s). Specific sugars of interest include, as illustrations, glucose, fructose, sucrose, maltose and other similar sugars for which the ampholytic base polymer has a relatively lower affinity than for the acid(s) to be separated.

Favored processes of the invention are conducted using a preparative-scale contacting apparatus including a plurality of resin columns and means for passing the admixed acid(s) and/or other compound(s) feed and eluent feed through the columns so as to establish separation and elution zones. A more preferred such apparatus is a continuous contacting apparatus ("CCA"). For example, continuous contacting apparatuses which are useful in the invention include those such as the ISEP or CSEP Continuous Contactors available from Advanced Separations Technology, Inc. (AST, Inc.), Lakeland, Fla., and are also generally described in U.S. Pat. No. 4,764,276 issued Aug. 16, 1988, U.S. Pat. No. 4,808,317 issued Feb. 28, 1989 and U.S. Pat. No. 4,522,726 issued Jun. 11, 1985. A brief description of such a CCA device as described in these patents is set forth below. For further details as to the design and operation of CCA's suitable for use in the invention, reference can be made to literature available from AST, Inc. including "The ISEP™ Principle Of Continuous Adsorption", and as well to the above-cited U.S. patents.

The preferred CCA for use in the present invention will be a liquid-solid contact apparatus including a plurality of chambers which are adapted to receive solid adsorbent material and which taken together or separately may provide a contacting zone for processes of the invention. The chambers have respective inlet and outlet ports, and are mounted for rotation about a central axis so as to advance the chambers past supply and discharge ports which cooperate with the inlet and outlet ports. In particular, liquid is supplied individually to inlet ports at the top of these chambers through conduits connected with a valve assembly above the chambers, which valve assembly provides a plurality of supply ports which cooperate with inlet ports of the chambers as they are advanced. Similarly, conduits connect the outlet port at the lower end of each chamber with a valve assembly below the chambers which provides discharge ports which cooperate with the outlet ports as the chambers are advanced. The valve assemblies include movable plates with slots that cover and uncover inlet ports as the plate rotates with the carousel. By varying the size of the slots in the plate and the location of the slots, the flow from the supply conduits into the chamber and flow from the chamber to the exhaust conduits can be controlled in a predetermined manner. The motion of one plate over the other can be continuous or as an indexed motion. The time during which liquid flows into and out of the chambers is a function of the speed of rotation of the chambers about the central axis.

More specifically, a preferred contacting device for use in the invention is shown generally in FIG. 1. The apparatus includes a rectangular frame 11 which supports a vertical drive shaft 12. A carousel 13 is mounted for rotation on the drive shaft. The carousel is fixed to the shaft and the shaft is driven by a motor 14 mounted on the frame 11. A plurality of cylindrical chambers 15 (e.g. 20 or 30 chambers) are mounted vertically on the carousel 13. The chambers are filled with the ampholytic base polymer. As shown at the left side of FIG. 1 in cross-section, the ampholytic base polymer 16 is preferably filled to about one-half or more of the height of the chamber 15. An arrangement is provided on each chamber 15 for inserting and removing the solid material through the top of the container. Pipe fittings 17 and 18 are provided at inlet and outlet openings on the top and bottom, respectively, of each chamber 15. An upper valve body 19 and a lower valve body 20 are mounted over the drive shaft 12. The valve bodies 19 and 20 provide supply and discharge ports, respectively (e.g. 20 each). Individual conduits 21 and 22 connect the valve bodies 19 and 20 with the respective upper and lower pipe fittings 17 and 18, so as to allow cooperation of the supply and discharge ports of valve bodies 19 and 20 with the inlet and outlet ports of the chambers 15. Supply conduits 23 (discharge is also possible) are mounted in the top of the frame 11 and extend upwardly from the valve body 19. Similarly, discharge conduits 24 (supply is also possible) extend downwardly from the lower valve body 19 to the frame 11. In this manner, as the carousel is rotated to advance the chambers 15, the inlet and outlet ports of the chambers 15 cooperate with the supply and discharge ports of the valve bodies 19 and 20 to provide advantageous means for circulating liquids through the chambers 15.

In accordance with one aspect of the invention, the apparatus of FIG. 1 will preferably be configured so as to include separation and elution zones. The separation zone can be conventionally operated so as to separate the acid, e.g. citric acid, from one or more other compounds over the ampholytic base polymer contained within chambers 15. Generally, the feed solution containing the acid(s) and/or other compound(s) will be passed countercurrent through the chambers 15 and over the resin. It will be understood that the number of ports of the CCA dedicated to the separation and elution zones may vary, and will be determined so as to maximize overall process economics. Specific illustrations of such configurations are discussed below in connection with the FIGS. 9 and 10.

In order to promote a further understanding of the present invention and its advantages, the following specific Examples are provided. It will be understood that these Examples are illustrative, and not limiting, of the invention. In these Examples, all percentages (%) given are by weight unless otherwise indicated.

EXAMPLE 1

Preparation of Acetate Quats

A 300 mL sample of Reillex™ HP polymer (Reilly Industries, Inc., Indianapolis, Ind. U.S.A.), 300 mL water, and 42.5 g monochloroacetic acid were combined in a 1 L round-bottomed flask equipped with reflux condenser, heating mantle and stirring paddle. The mixture was heated slowly over 6 hours to 85° C. and held at this temperature for an additional 17 hours, and then cooled and filtered. The resin was washed with several bed volumes of water, several bed volumes of dilute caustic solution (5% NaOH) until the filtrate tested basic, then again with several bed volumes water. An infrared spectra of a dried sample of the off-white beads showed complete conversion to the acetate derivative.

An analogous procedure was used except replacing the Reillex™ HP resin with Amberlite IRA 93 resin, to prepare the corresponding completely-converted IRA 93 acetate quat.

A 50% quaternized Reillex™ HP acetate quat was prepared as a 500.0 mL sample of Reillex™ HP polymer (poly-4-vinylpyridine, divinylbenzene) was combined with ca. 1000 mL of dry methanol, 37.8 g of chloroacetic acid in 75.0 mL of methanol, and heated at reflux temperature for seven hours. The polymer was transferred to a column and washed with methanol (1000 mL), water (1500 mL), 5% aqueous ammonium hydroxide solution (1500 mL), and water (1500 mL). Infrared spectroscopy showed approximately 50% of the available sites in the polymer were converted.

EXAMPLES 2–7

Pulse Tests with Acetate Quat of Crosslinked Polyvinylpyridine

Figure 8:
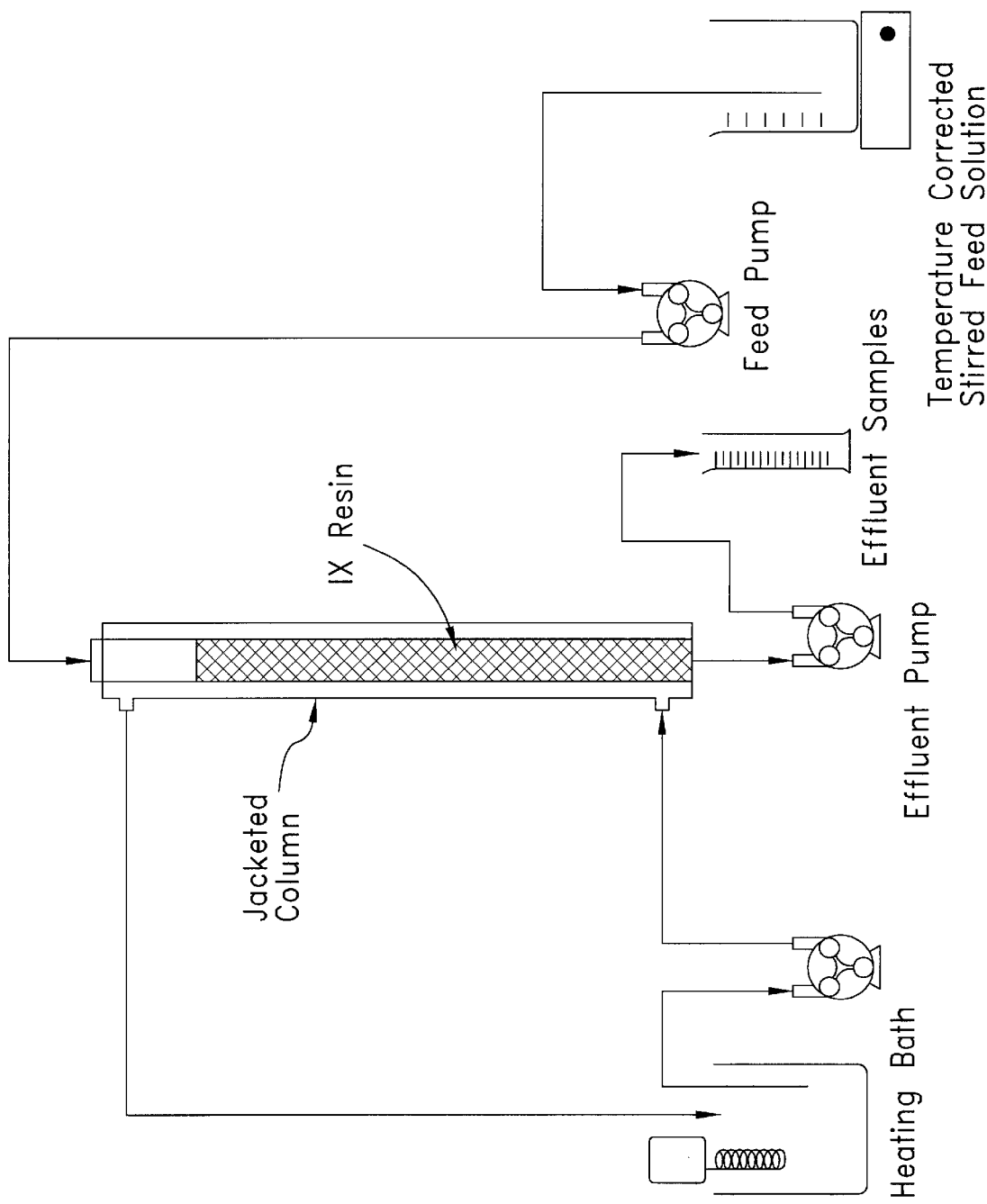
FIG. 8 is a schematic diagram of the column setup employed in the pulse testing of Examples 2–7 below.

A series of pulse tests was carried out using a 1.0 inch inner diameter jacketed chromatography column equipped as shown in FIG. 8 filled with a fully quaternized Reillex™ HP acetate quat resin (Examples 2a, 2b and 5), the 50% quaternized Reillex™ HP acetate quat resin (Examples 3 and 4), or the IRA 93 acetate quat resin (Examples 6–7) prepared as in Example 1 in water (final backwashed and settled resin bed volume=230 mL). The system was set with the desired feed flow rate and jacket temperature. A solution of citric acid and glucose was fed to the top of the resin bed and immediately eluted with water. Samples were collected from the bottom of the column at the start of the feed solution and analyzed by HPLC for citric and glucose. The parameters for the several Examples and the results are shown in Table 1 below and in the correspondingly-numbered Figures, which show chromatograms plotted for the various runs.

TABLE 1

| Ex | Feed % Citric/ % Glucose | Feed Wt. (g) | Feed Vol. (mL) | Flow Rate (mL/min) | Elution Temp. (° C.) | FIG. |
|---|---|---|---|---|---|---|
| 2a | 50/1 | 49.3 | 44.0 | 15.1 | 85 | 2 |
| 2b | 50/1 | 49.3 | 44.0 | 15.1 | 25 | 2 |
| 3 | 50/1 | 49.3 | 44.0 | 15.1 | 85 | 3 |
| 4 | 50/1 | 49.3 | 44.0 | 15.1 | 25 | 4 |
| 5 | 35/10* | 49.3 | 44.0 | 15.1 | 85 | 5 |
| 6 | 50/1 | 49.3 | 44.0 | 15.1 | 85 | 6 |
| 7 | 50/1 | 49.3 | 44.0 | 15.1 | 25 | 7 |

*Also containing 2% malic acid.

As demonstrated by FIGS. 2–7, the ampholytic base polymers effectively separate citric acid and glucose.

EXAMPLE 8

Isothermal Run in Continuous Contacting Apparatus

Figure 9:
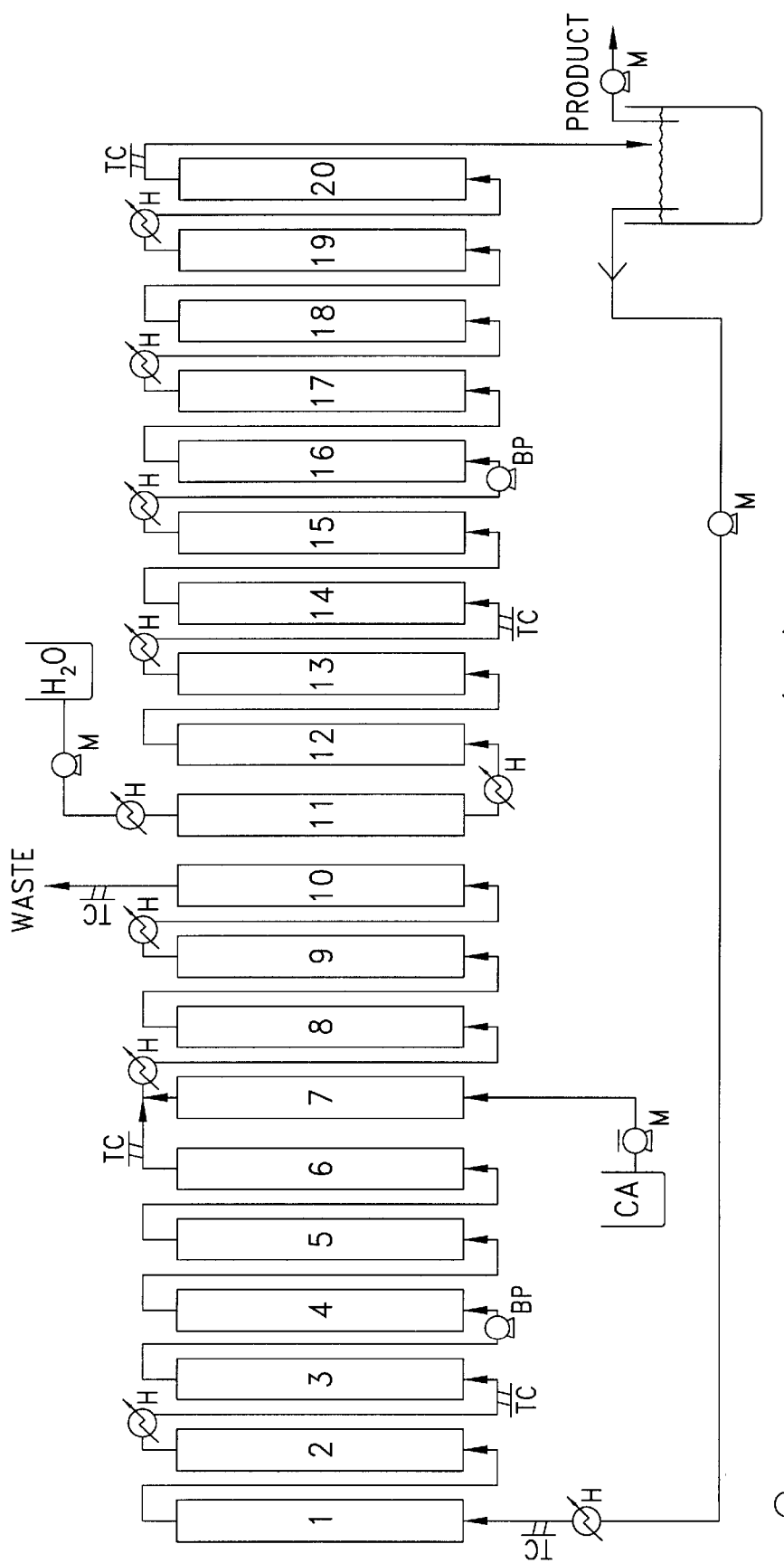
FIGS. 9 and 10 are schematic diagrams of port configurations for testing in a continuous contacting apparatus, as described in Examples 8–11 below.

A 20 port/20 bed C920 moving bed contactor manufactured by AST, Inc. of Lakeland, Fla., USA, was equipped with pumps, heat exchangers and piping according to the schematic shown in FIG. 9. The 20 columns were filled with the fully quaternized Reillex™ HP acetate quat resin (Example 1) in water (total bed volume=4400 mL). A feed solution (85° C.) of 50% citric acid and 2% glucose was introduced to the system at a flow rate of 10.3 mL/min. Water (85° C.) was introduced as the eluent at a flow rate of 61.5 Ml/min. The "step time" for the resin columns, i.e. the period of time which the resin columns remained at a given port before moving to the next, was set at 330 seconds. The system was run for about 5 hours to allow equilibration, after which samples of product streams were pulled and analyzed. In time-averaged results, this setup produced a citric product stream containing 19.45% by weight citric acid, and 0.08% glucose, and a sugar waste stream containing 0.13% by weight citric acid and 0.43% by weight glucose. The total mass balance for the system was 99.3%, with a citric acid recovery of 99.3% and a glucose rejection of 83.8%.

EXAMPLE 9

Isothermal Run in Continuous Contacting Apparatus

The procedure of Example 8 was repeated, except using a citric acid feed containing 50% citric acid, 1% glucose, 1% maltose, 0.05% potassium sulfate, and 0.05% calcium sulfate, a citric acid feed rate of 10.2 mL/min and an eluent feed rate of 61.2 mL/min. In time-averaged results, this setup produced a citric product stream containing 18.4% by weight citric acid, 0.07% glucose, 0.02% maltose, 2.0 ppm potassium and 8.4 ppm calcium. The waste stream contained 0.18% by weight citric acid, 0.20% by weight maltose, 0.22% by weight glucose, 55 ppm potassium and 40 ppm calcium. The total mass balance for the system was 99%, with a citric acid recovery of 99%, a glucose rejection of 77%, a maltose rejection of 92%, a sugar (RCS) rejection of 85%, a potassium rejection of 97% and a calcium rejection of 83%.

EXAMPLE 10

Separation/elution Thermal Swing in CCA

The procedure of Example 8 was repeated, except the citric acid/glucose feed was cold (about 25° C.). The citric product stream contained 19.6% citric acid and 0.08% by weight glucose, and the waste stream contained 0.14% citric acid and 0.44% glucose. Total mass balance for the system was 99.7%, citric recovery was 99.2% and glucose rejection was 85.3%.

EXAMPLE 11

Isothermal Run In CCA

Figure 10:
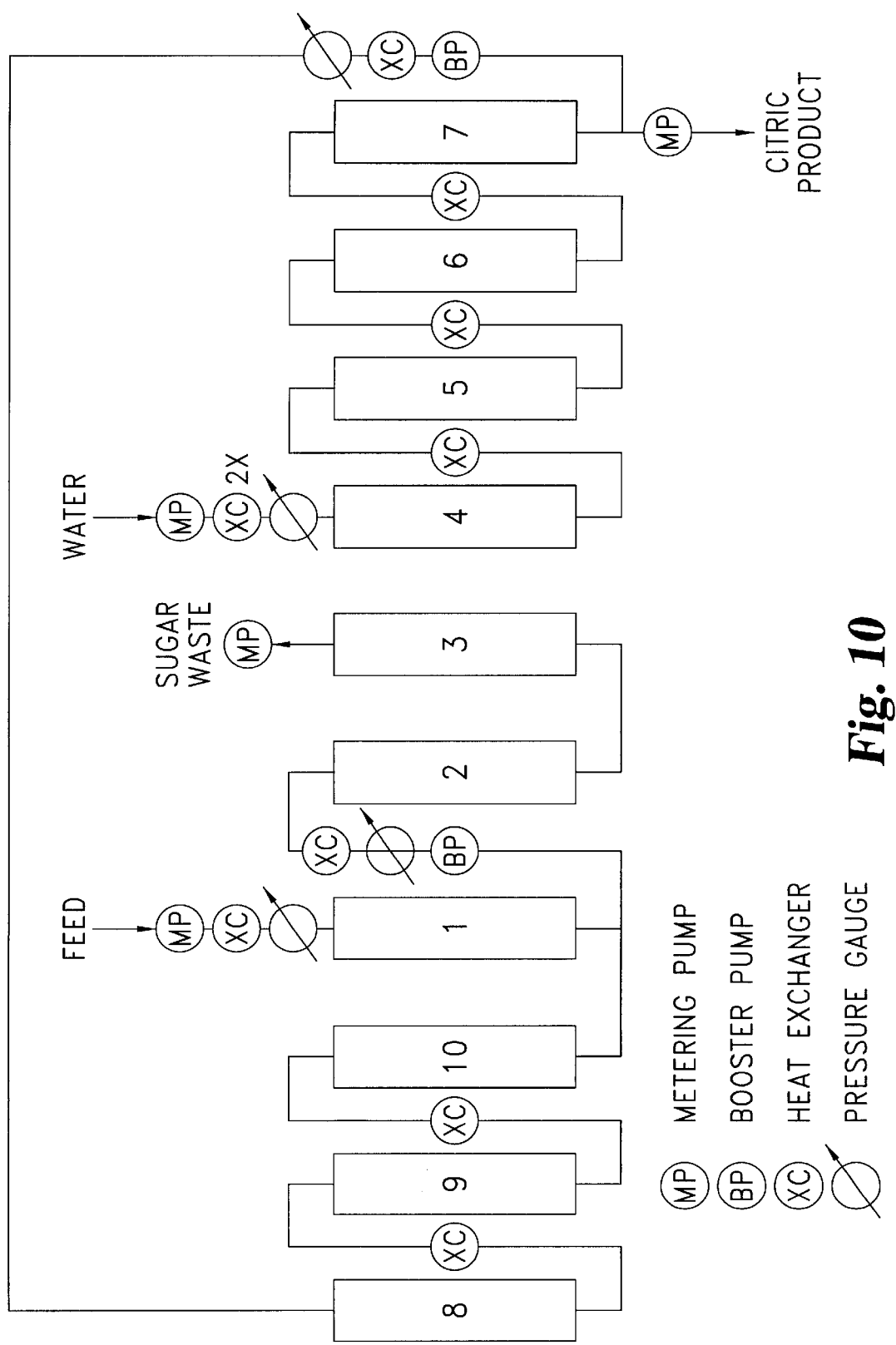

The procedure of Example 9 was repeated, except the feed contained 0.1% potassium sulfate instead of 0.05%, the citric feed rate was 12.6 mL/min, the water eluent rate was 61 mL/min, and the CCA configuration was changed to that shown in FIG. 10. The citric product stream contained 20.9% citric acid, 0.1% glucose, and 0.02% maltose. The sugar waste stream contained 0.52% citric acid, 0.17% glucose and 0.29% maltose. Potassium and calcium levels in the citric product and sugar waste streams were not assayed in this run. The total mass balance was 98.8%, the citric recovery was 97.5%, the glucose rejection was 61.2%, the maltose rejection was 94%, and the sugar (RCS) rejection was 65.3%.

EXAMPLE 12

Use of Ethanol Eluent

The procedure of Example 11 was repeated, except using ethanol as the eluent, a citric feed flow rate of 10.0 mL/min and an eluent flow rate of 61.2 mL/min. The resulting citric product stream contained 17.9% citric acid, 0.3% glucose, and 0.2% maltose. The sugar waste stream contained 2.6% citric acid, 0.14% glucose and 0.18% maltose.

EXAMPLE 13

Preparation of Sulfonate Quat

A 500 ml sample of toluene wet Reillex™ HP resin, 122.1 g (1 mole) 1,3-propanesultone and 1500 ml of toluene were combined and heated at reflux temperature for 40 hours. The resin was then collected by filtration and washed with methanol, water and 5% NaCl-1% NaOH solution. The product was confirmed by FTIR.

EXAMPLE 14

Preparation of Pyridine N-Oxide Form

A 1000 ml sample of water wet Reillex™ HP resin and 1500 ml water, 1 ml conc, $H_2SO_4$ in 15 ml of water were combined and brought to reflux temperature. To this mixture was added 315.4 g of 35% $H_2O_2$ dropwise over 5 hours. Heating was continued for 16 hours. Then an additional 50 g 35% $H_2O_2$ were added and heating was continued for an additional 24 hours. The resin was collected by filtration and washed with water to yield a pale yellow resin. The product was confirmed as Reillex™ HP N-Oxide by FTIR.

EXAMPLE 15

Preparation of Acetylacetone Quat

A 10 ml sample of water wet Reillex™ HP resin, 150 ml isopropanol and 2.7 g 3-chloro-2,4-pentanedione were combined and heated at reflux temperature for 5 hours. The resin was then collected by filtration and washed extensively with methanol. The product was confirmed by FTIR.

EXAMPLE 16

Preparation of Acetate Quat of IRA-93

A 400 ml (270.2 g) sample of Amberlite IRA-93 resin, 1000 ml water and 150 g (1.59 moles) chloroacetic acid in 1000 ml water were combined and heated at 45° C. for 6 hours. The resin was collected by filtration and then washed with methanol and water. The product was confirmed by FTIR.

EXAMPLE 17

Preparation of Carboxyl Acetate Pyridine Quat

A 400 ml sample of water wet Reillex™ HP resin, 2000 ml methanol and 184 g (0.77 moles) diethylbromo malonate were combined and heated at reflux temperature for 7 hours. The resulting yellow resin was isolated by filtration, washed with methanol, and water, and 5% HCl solution. The resin was then combined with 1.5 L 10% HCl and heated at reflux temperature for 18 hours. The resin was isolated by filtration, and washed with water, and with 5% NaCl-1% HaOH solution, and with 5% NaCl solution, and again with water to yield the final product as a green solid. The product was confirmed by FTIR.

EXAMPLE 18

Epichlorohydrin Quat

A 100 mL sample of Reillex™ HP polymer (poly-4-vinylpyridine, divinylbenzene) was combined with 100.00 mL of water and 10.2 g of epichlorohydrin dropwise and stirred for six hours at 25° C., then washed with several bed volumes of water to yield the product as dark pink beads.

EXAMPLE 19

Reaction of Epichlorohydrin Quat with Sodium Bisulfate to form Hydroxyl Sulfate Quat A 50.0 mL sample of Reillex™ HP polymer with Epichlorohydrin was combined with 10.4 g of sodium bisulfite and 100.0 mL of water and heated with stirring at 80° C. for approximately five hours. The resin was washed with several bed volumes of water to yield the product as light gray beads.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

All publications cited herein are indicative of the level of skill in the art and are hereby incorporated by reference as if each had been individually incorporated by reference and fully set forth.

What is claimed is:

1. A crosslinked, bead form ampholytic base polymer which is at least 15 weight % crosslinked, said polymer not swelling to an appreciable extent and having repeating units of the formula:

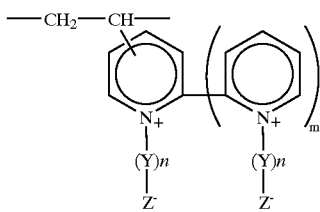

wherein:
- m and n are each 0 or 1;
- Y is a linking group covalently linking $N^+$ and $Z^-$ and $Z^-$ is a negatively-charged group, with the proviso that when $—Z^-$ is $O^-$, n is 1.

2. The polymer of claim 1, which has repeating units encompassed by the formula:

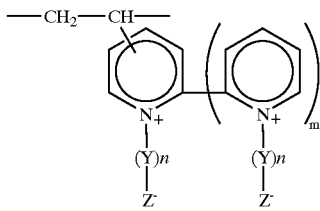

wherein:
- m and n are defined as in claim 1; and
- Y is an alkylene group having from 1 to about 6 carbon atoms.

3. The polymer of claim 2, wherein n=1, and $Z^-$ is $CO_2^-$.

4. The polymer of claim 3, wherein m=0.

5. The polymer of claim 4, wherein Y is $—CH_2—$.

6. The polymer of claim 2, which is a modified polyvinylpyridine resin.

7. The polymer of claim 6, which is a modified poly-2-vinylpyridine or poly-4-vinylpyridine resin.

8. The polymer of claim 7, which is 15 to 50 weight % crosslinked with divinylbenzene.

9. A crosslinked, bead-form ampholytic base polymer which is 15 to 50 weight % crosslinked, having repeating units encompassed by the formula:

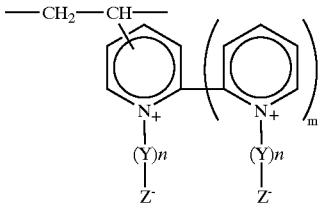

wherein:
- m and n are each 0 or 1;
- Y is a linking group covalently linking $N^+$ and $Z^-$, and $Z^-$ is a negatively-charged group, with the proviso that when $—Z^-$ is $—O^-$, n is 1.

10. The polymer of claim 9, wherein,
- m and n are as defined in claim 9; and
- Y is an alkylene group having from 1 to about 6 carbon atoms.

11. The polymer of claim 10, wherein n=1, and $Z^-$ is $CO_2^-$.

12. The polymer of claim 11, wherein m=0.

13. The polymer of claim 12, wherein Y is $—CH_2—$.

14. The polymer of claim 10, which is a modified polyvinylpyridine resin.

15. The polymer of claim 14, which is a modified poly-2-vinylpyridine or poly-4-vinylpyridine resin.

16. The polymer of claim 15, which is crosslinked with divinylbenzene.

* * * * *

UNITED STATES PATENT AND TRADEMARK OFFICE
CERTIFICATE OF CORRECTION

PATENT NO.    : 6,420,439 B1
DATED         : July 16, 2002
INVENTOR(S)   : Martin Grendze et al.

Page 1 of 1

It is certified that error appears in the above-identified patent and that said Letters Patent is hereby corrected as shown below:

Title page,
The second reference under OTHER PUBLICATIONS, please change "Cook" to -- Book --.
The second reference under OTHER PUBLICATIONS, please change "105" to -- 102 --.

Column 2,
Line 49, please change "z" to -- Z --.

Column 4,
Line 33, please move "+" to line 32 before and slightly above "$NH_3$".

Column 7,
Line 39, please move "+" to line 38 before and slightly above "$NH_3$".

Signed and Sealed this

Twenty-sixth Day of November, 2002

Attest:

JAMES E. ROGAN
Attesting Officer
Director of the United States Patent and Trademark Office